US00PP25235P3

(12) United States Plant Patent
Preil

(10) Patent No.: US PP25,235 P3
(45) Date of Patent: Jan. 20, 2015

(54) ***RHODODENDRON* ROOTSTOCK NAMED 'RHODUNTER 150'**

(50) Latin Name: ***Rhododendron* hybrid**
Varietal Denomination: Rhodunter 150

(71) Applicant: Inkarho GmbH, Bad Zwischenahn (DE)

(72) Inventor: Walter Preil, Ammersbek (DE)

(73) Assignee: Inkarho GmbH, Bad Zwischenahn (DE)

( * ) Notice: Subject to any disclaimer, the term of this patent is extended or adjusted under 35 U.S.C. 154(b) by 0 days.

(21) Appl. No.: 13/694,107

(22) Filed: Oct. 30, 2012

(65) Prior Publication Data
US 2014/0123354 P1 May 1, 2014

(51) Int. Cl.
*A01H 5/00* (2006.01)

(52) U.S. Cl.
USPC ..... Plt./238

(58) Field of Classification Search
USPC ..... Plt./238
See application file for complete search history.

*Primary Examiner* — Anne Grunberg
(74) *Attorney, Agent, or Firm* — The Webb Law Firm

(57) ABSTRACT

A new and distinct *Rhododendron* hybrid plant used as a rootstock that exhibits a high lime tolerance and vigorous growth.

1 Drawing Sheet

Botanical classification: *Rhododendron* hybrid.
Varietal denomination: 'Rhodunter 150'.

BACKGROUND OF THE INVENTION

The present invention comprises a new and distinct cultivar of *Rhododendron* hybrid used as a rootstock known by the varietal name 'Rhodunter 150'. The new variety was discovered in Ahrensburg, Germany. The new variety is the result of a planned breeding program between an unnamed and unpatented *Rhododendron fortunei* variety (female parent) and *Rhododendron* cv. 'Cunningham's White' (unpatented male parent). 'Rhodunter 150' exhibits leaves and flowers that are more similar to its female parent than to its male parent. Additionally, 'Rhodunter 150' exhibits more vigorous growth when compared to its male parent. Further, the new variety differs from both parents in its improved tolerance to lime. In fact, such improved lime tolerance (no Fe-deficiency symptoms on soils up to 6.9 pH) distinguishes the new variety from other *Rhododendron* varieties known to the breeder and satisfied the purpose of the breeding program. 'Rhodunter 150' has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type:

FIG. 1 shows a view of the new variety grown to a flowering plant.

DESCRIPTION OF THE PLANT

The following detailed description sets forth the characteristics of the new cultivar. The data which defines these characteristics were collected by asexual reproductions performed via cuttings or in vitro culture carried out in Ahrensburg, Germany. The color readings and measurements were taken outside under natural daylight on plants grown in containers. Color references are primarily to The R.H.S. Colour Chart of The Royal Horticultural Society of London.

PLANT

Time to develop roots: About 90 days at 22-25° C.
Time to produce a finished flowering plant from a rooted cutting: About 4 years in the field.
Rooting habit: Spreading.
Height: 50 cm. at 3 years.
Diameter: 40 cm. at 3 years.
Vigor: Strong.
Branching habit: Compact.
Disease, temperature, and drought resistance: No observations made to date.
Trunk:
- *Diameter.*—3 cm. at 5 cm. above soil height at 4 years.
- *Bark color.*—174A to 174C.
- *Texture.*—Hard.
- *Pubescence.*—Absent.
- *Form.*—Erect.

Lateral branches:
- *Diameter.*—5-7 mm.
- *Internode length.*—1-2 cm.
- *Texture.*—Hard.
- *Pubescence.*—Absent.
- *Color.*—174A to 174C.

Leaves:
- *Nature.*—Evergreen.
- *Arrangement.*—Alternate.
- *Length.*—15 cm. maximum.
- *Width.*—5.5 cm. maximum.
- *Shape.*—Oblanceolate.
- *Apex.*—Broad.
- *Base.*—Tapering.
- *Margin.*—Entire.
- *Texture.*—Hard.

*Pubescence*.—Absent.

*Color*.—Upper surface: 147B for young leaves and 147A for mature leaves. Lower surface: 147C for both young and mature leaves.

*Margins*.—Entire.

*Venation pattern*.—Dense venation with a pronounced central vein.

*Vein color*.—Upper surface: 144A. Lower surface: 145C.

*Stipules*.—None present.

*Bracts*.—None present.

*Pedicels*.—General description: Round. Length: 3-5 cm. Diameter: 1.5-2 mm. Color: 145A.

*Petiole*.—Length: 3 cm. Diameter: 4-5 mm. Color: 147C.

Flower:

*Natural flowering season*.—Beginning of May until the end of May in Northern Germany.

*Form*.—Round spike.

*Lastingness of bloom*.—From one to two weeks.

*Average number of blooms on a plant*.—Approximately 20 on a plant with a diameter of 40 cm.

*Fragrance*.—Typical of Rhododendron fortunei.

*Buds* (*described before bursting*).—Shape: Oblong. Width: 20 mm. Length: 40 mm. Color: 34C.

*Spike*.—Number of flowers per spike: 10-15. Length: 15 cm. Diameter: 15 cm.

*Corolla petals*.—Form: Zygomorphic. Shape: Widely funnel-shaped. Number: 7. Length: Approximately 55 mm. Width: Approximately 50 mm. Margin: Undulate. Texture: Wax-like. Color (both surfaces): 11B when opening and fully opened.

*Corolla throat*.—Tube length: Approximately 20 mm. Color: 1C. Texture: Wax-like.

*Sepals*.—Fused; 144B in color.

Reproductive organs:

*Stamens*.—Number: 14.

*Filament length*.—Approximately 30 mm.

*Anthers*.—Shape: Normal Rhododendron type. Color: 11B. Length: 5 mm.

*Pollen*.—Amount of pollen: Average. Color of pollen: 158C.

*Pistil*.—Number: 1. Length: Approximately 35 mm. Style: Color: 150B. Length: Approximately 30 mm.; filiform. Stigma: Shape: Undivided. Color: 145A.

Seeds:

*Production*.—Seed capsules mature in November when pollinated in May.

*Length*.—2 mm.

*Color*.—167B to 167C.

*Number*.—Approximately 200 per capsule.

I claim:

1. A new and distinct variety of *Rhododendron* hybrid plant, as is herein illustrated and described.

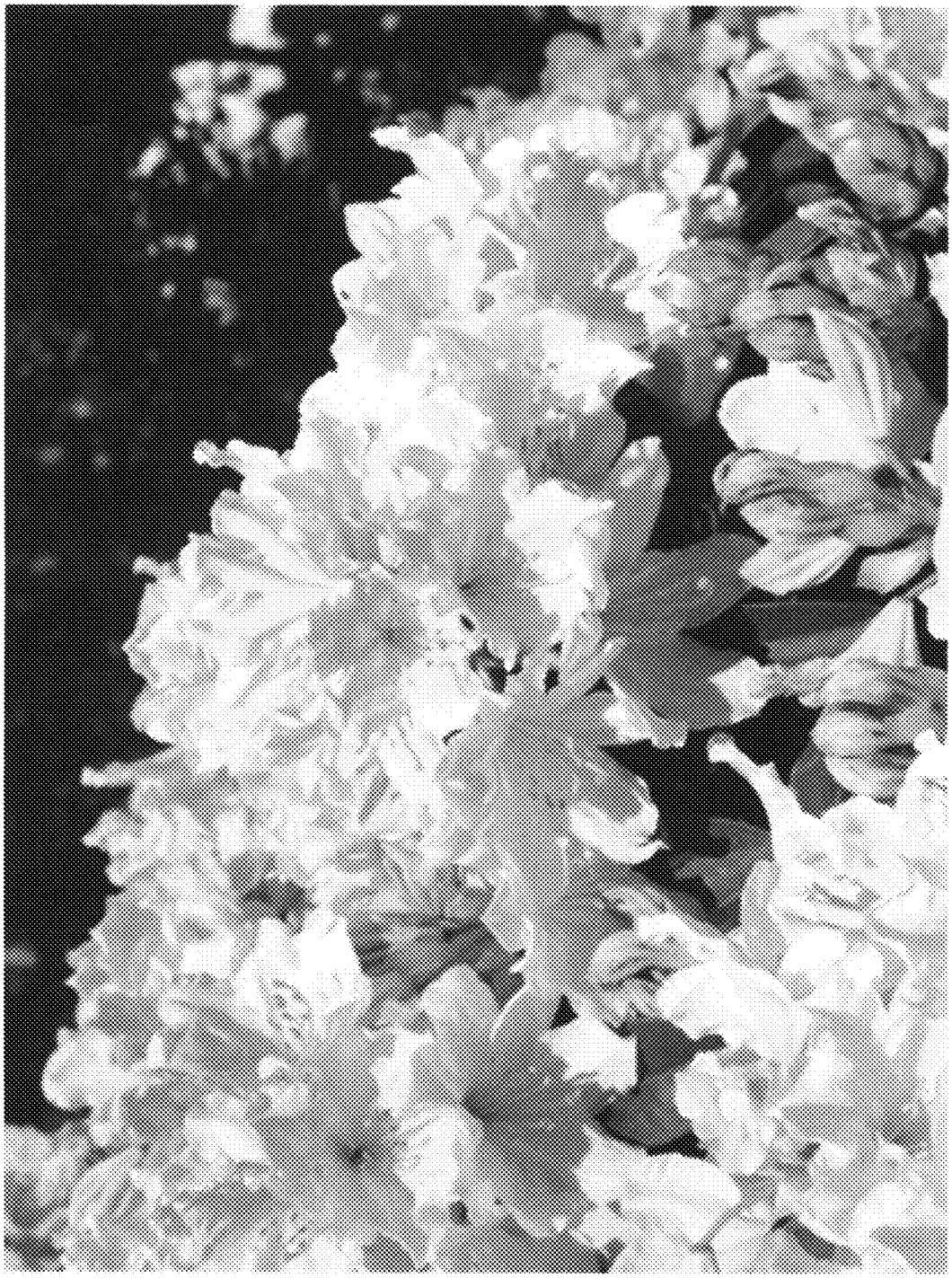

* * * * *